United States Patent
Li (10) Patent No.: US 7,397,027 B2
(45) Date of Patent: Jul. 8, 2008

(54) MULTI-CHANNEL HIGH-FIELD ASYMMETRIC WAVEFORM ION MOBILITY SPECTROMETRY

(75) Inventor: Gangqiang Li, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 242 days.

(21) Appl. No.: 11/442,250

(22) Filed: May 30, 2006

(65) Prior Publication Data

US 2008/0067350 A1    Mar. 20, 2008

(51) Int. Cl.
B01D 59/46    (2006.01)
(52) U.S. Cl. .................. 250/287; 250/281; 250/282; 250/285; 250/288; 250/292
(58) Field of Classification Search ............ 250/281, 250/282, 285, 287, 288, 292
See application file for complete search history.

(56) References Cited

U.S. PATENT DOCUMENTS 6,806,466 B2    10/2004    Guevremont et al.
6,815,668 B2    11/2004    Miller et al.
6,825,461 B2    11/2004    Guevremont et al.
2004/0094704 A1*    5/2004    Miller et al. ............... 250/287

OTHER PUBLICATIONS

Buryakov, I.A., et al., "A new method of separation of multi-atomic ions by mobility at atmospheric pressure using a high-frequency amplitude-asymmetric strong electric field", Int. Journal of Mass Spectrometry & Ion Processes, vol. 128 (May 18, 1993) pp. 143-148.
Guevremont, Roger, et al., "Atmospheric pressure ion focusing in a high-field asymmetric waveform ion mobility spectrometer", Review of Scientific Instruments, vol. 70, No. 2 (Oct. 27, 1998) pp. 1370-1383.

* cited by examiner

Primary Examiner—Jack I. Berman
Assistant Examiner—Michael Maskell (57) ABSTRACT

A multi-channel high field asymmetric waveform ion mobility spectrometer (FAIMS) is provided. The apparatus provides for substantially simultaneous FAIMS analysis of plurality of ions from a single sample. The apparatus has a analyzer region comprising a hollow electrode, a plurality of plate electrodes positioned parallel to and distanced from the hollow electrode, a contact for applying an high voltage asymmetric waveform to the hollow electrode and a plurality of contacts for applying a compensation voltage to the plurality of plate electrodes. A method for substantially simultaneous FAIMS analysis of plurality of ions from a single sample is also provided.

22 Claims, 6 Drawing Sheets

MULTI-CHANNEL HIGH-FIELD ASYMMETRIC WAVEFORM ION MOBILITY SPECTROMETRY

TECHNICAL FIELD

The invention relates generally to ion analysis and more particularly to ion analysis in ion mobility spectrometry.

BACKGROUND

High-Field Asymetric Waveform Ion Mobility Spectrometry (FAIMS) is a technology useful both for the separation of gas-phase ions at atmospheric pressure and room temperature as well as separation of gas phase ions over a wide range of temperatures and pressures.

In general, FAIMS is characterized by several features. These features include:

(1). Strong electric fields are used in FAIMS. Typically, FAIMS operates with fields greater then 5,000 volts/cm.

(2). In FAIMS a periodic asymmetric electric waveform is applied to conductive surfaces (e.g., plates) about 1-4 mm apart. The electric waveform is asymmetric which means that there is a significant difference between the peak +Ve and the peak −Ve voltage during the applied waveform. Either the +Ve or the −Ve may be the higher voltage.

(3). In FAIMS ions move through a gas in the electric field generated by the periodic asymmetric electric waveform. The gas is sufficiently dense that the ions rapidly reach a terminal velocity that is roughly proportional to the strength of the electric field. The velocity is compound dependent, permitting the separation of ion species from each other. The ions drift toward one of the plates as they travel in the electric field. Typically this drift may be stopped by applying a small DC voltage known as a compensation voltage (CV) which allows an ion specie of a selected mobility to pass through the field region to a detector.

A conventional FAIMS device permits sequential detection of different species of ions (e.g., ions having different mobilities) but does not provide for simultaneous analysis and/or detection of a plurality of ion species simultaneously.

Accordingly, there is a need for a FAIMS device and method for substantially simultaneous analyses and detection of a plurality of ion species.

SUMMARY

A high field asymmetric waveform ion mobility spectrometer apparatus for separating ion species is disclosed. The apparatus comprises an analyzer region having a hollow electrode with external surfaces and a central region and a plurality of plate electrodes. The plate electrodes are positioned parallel to and distanced from a surface of the hollow electrode so as to form a plurality of ion channels with a channel formed between each plate electrode of the plurality of plate electrodes and the hollow electrode. The apparatus further comprises a contact for applying an asymmetric waveform to the hollow electrode, and a plurality of contacts for applying a compensation voltage to each of the plurality of plate electrodes. The compensation voltage is independently adjustable to each of the plurality of plate electrodes. The apparatus may further comprise an ion source and a detection system in communication with the analyzer region. The detection system may detect a plurality of ion species substantially simultaneously. The hollow electrode may have a polygonal shape and planar plate electrodes or alternatively the hollow electrode may be cylindrical and have curved plate electrodes.

A method for separating ions species is disclosed. The method comprises the steps of providing a plurality of ion species and providing an analyzer including an analyzer region comprising a hollow electrode having a surface and a plurality of plate electrodes arranged parallel to and distanced from the surface of the hollow electrode thereby creating a plurality of channels. A channel is formed between each plate electrode and the surface of the hollow electrode. The method further includes applying a high voltage asymmetric waveform to the hollow electrode to generate a field in the plurality of channels between the hollow electrode and the plurality of plate electrodes. The high field asymmetric waveform is set at a voltage sufficient to effect a difference in net displacement between a first and a second ion species of the plurality of ion species in the time of one cycle of the applied asymmetric waveform. A first compensation voltage is provided to a first plate electrode of the plurality of plate electrodes and a second compensation voltage is provided to a second plate electrode of the plurality of plate electrodes. The first compensation voltage to the first plate electrode of the plurality of plate electrodes is set to a determined value to support transmission of the first ion species through a first channel between the first plate electrode and the hollow electrode and the second compensation voltage to the second plate electrode of the plurality of plate electrodes is set to support transmission of the second ion species through a second channel between the second plate electrode and the hollow electrode. The first and the second ion species may be detected substantially simultaneously upon transmission though the first and the second channels.

DETAILED DESCRIPTION

The present invention provides a FAIMS apparatus and method for substantially simultaneous detection of a plurality of ion species. The apparatus is a multi-channel FAIMS device which provides for substantially simultaneous analysis and detection of a plurality of ion species from a single sample in real time. Simultaneous detection of a plurality of ion species provides advantages of increased speed of analysis, improved efficiency of sample utilization, and real time comparisons of abundance of selected ion species. Substantially simultaneous detection includes both actual detection of a plurality of ion species at precisely the same time and the capability to detect a plurality of ion species at the same. Accordingly, substantially simultaneous detection does not require that the initiation and/or duration of the detection be the same for all ion species detected. For example, detection of one ion species may be in progress when detection of a second ion species is begun.

Figure 1:
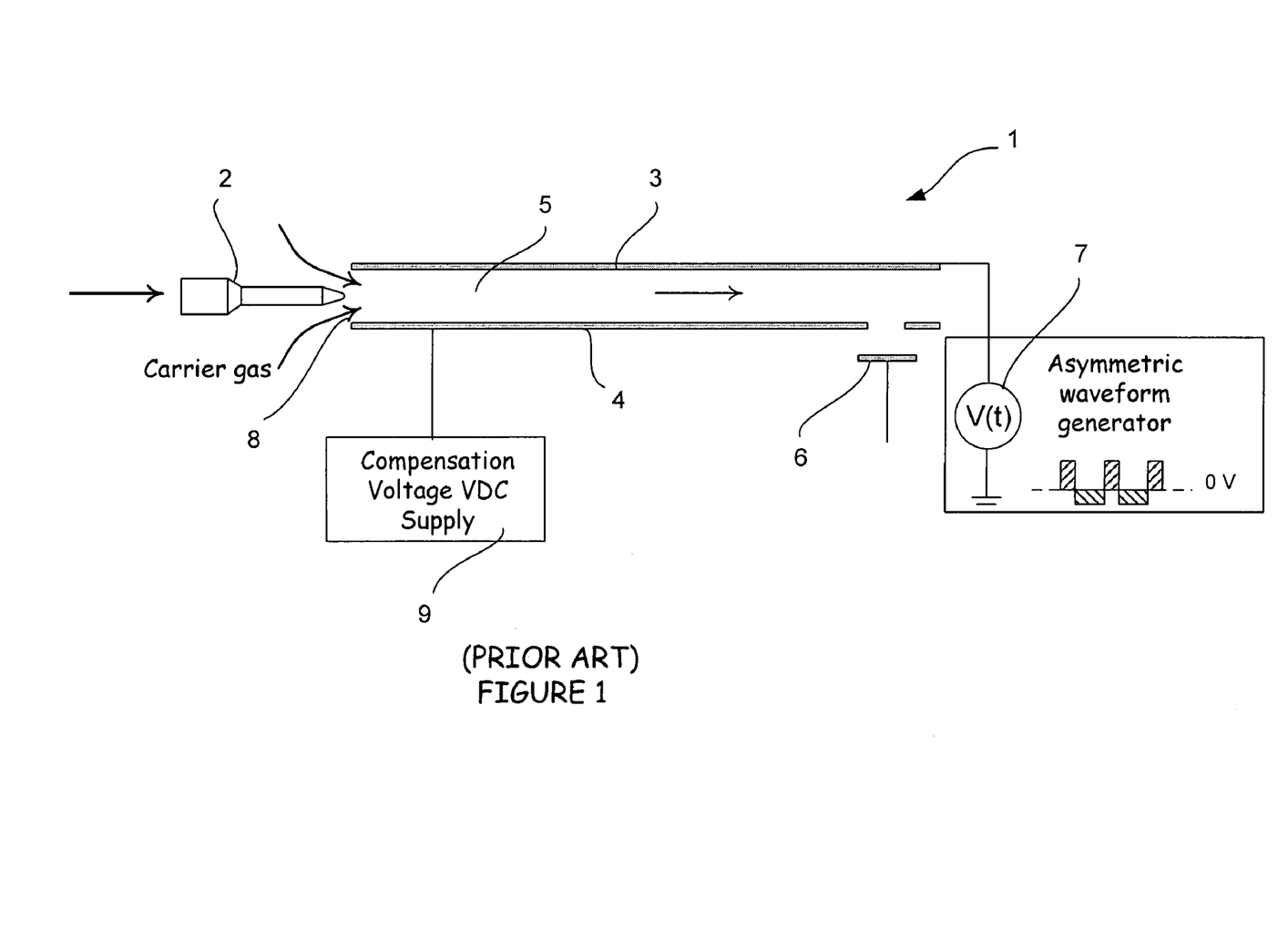
FIG. 1 is a cross sectional view of a prior art FAIMS spectrometer.

A schematic diagram of a conventional prior art FAIMS apparatus is shown in FIG. 1. Referring to FIG. 1, the conventional FAIMS apparatus 1 includes an ion source 2, a pair of parallel planar plate electrodes 3, 4, an ion channel 5, an ion detector 6, an asymmetric waveform generator 7, a carrier gas entrance orifice 8, and a compensation voltage generator 9.

In a conventional FAIMS spectrometer such as the prior art example of FIG. 1, a plurality of ions species from the ion source are introduced into the ion channel 5 (e.g. the "channel" or the region between the two parallel planar plate electrodes 3, 4). An ion species is an ion with recognizable distinctive or characteristic features of composition and/or charge. The plurality of ion species are introduced into a stream of carrier gas which is admitted to the ion channel 5 via carrier gas entrance orifice 8. Typically, nitrogen, oxygen, or $CO_2$ is used as the carrier gas. However, other gases or gas mixtures may be used. Typically, a gas with a low propensity for chemical reaction with the ions of interest is preferred. As ions travel in the stream of carrier gas between the plate electrodes 3, 4, the asymmetric waveform generator 7 applies an asymmetric high voltage waveform to one of the plate electrodes 3. The waveform generates a time dependent high-field (e.g. typically, a field greater than 5000 volts/cm). The high field causes ions traveling in the ion channel 5 to drift towards to the opposite plate electrode 4. Absent other forces, ions will collide with opposite the plate electrode 4 and fail to pass through the channel (e.g., ion channel 5) defined by the plate electrodes 3, 4.

The degree of drift depends on the mobility character of a particular ion species in the carrier gas. Ion size, chemical composition and charge are exemplary of the factors that determine the ion mobility characteristic of a specific species of ions and accordingly degree of drift. If a DC voltage (e.g., compensation voltage or CV) is applied to the electrode opposite the electrode to which the asymmetric waveform is applied (e.g., plate electrode 4 in the example of FIG. 1), a compensation field is generated. In the presence of the additional compensation field, ions are forced to move in a direction opposite the initial drift. With an appropriately chosen compensation voltage (namely, selection of a CV with suitable polarity and magnitude), the movement of a single species of ions with a particular selected mobility character is balanced between the two plate electrodes and the selected ion specie can migrate to the ion detector 6. Other species of ions of the plurality of ion species in the sample having different mobility character hit one of the plate electrodes 3, 4 and become discharged.

A detector 6 is placed at the end of the apparatus 1 opposite the ion source 2 to receive the selected species of ions that pass through the length of the ion channel 5. The ion detector 6 may be positioned off axis as shown in FIG. 1 or optionally in the line of flow of the carrier gas as the gas exits the ion channel 5.

Typically, when a beam of a mixture of ion species is introduced into the conventional FAIMS spectrometer from the ion source 2 though a sample inlet, either the compensation voltage is set to transmit a selected ion species of interest and monitor it for a period of time or the compensation voltage is varied with time (scanned) so that ions of different compounds sequentially pass through the ion channel 5 between the plate electrodes 3, 4 to the detector 6. Detecting species of ions sequentially yields an ion mobility spectrum as a function of the compensation voltage.

In the conventional FAIMS spectrometer for a given compensation voltage, only a single ion species with a specific particular ion mobility characteristic can pass through the ion channel 5 and be detected at a given time. Other species of ions in the sample are lost. Such losses reduce the instrument efficiency and sensitivity. As indicated, the compensation voltage may be adjusted in a predetermined systematic manner (e.g., scanned) to provide for sequential detection of a plurality of ion species. However, "scanning" does not provide for simultaneous detection of multiple ion species. Further, simultaneous detection is desirable when a FAIMS is utilized for detecting transient signals such as signals generated by a gas chromatograph or a liquid chromatograph or when FAIMS is used for real time monitoring in an industrial or environmental application where multiple ion species are of interest, for example.

The embodiments provide an apparatus and a method for substantially simultaneously detecting a plurality of individual ion species in a mixture of ion species in which the ion species of the mixture have different ion immobilities. The apparatus and method provide for substantially simultaneous detection of a plurality of ion species without scanning the compensation voltage, hence, the speed of analysis may be increased several fold over conventional FAIMS in applications in which multiple ion species are of interest. As the apparatus and method provide for efficient use of ions, in some embodiments a significant increase in analytical sensitivity can be achieved. Further, substantially simultaneous ion detection may provide the ability to monitor a rapid change in sample composition, a feature that is useful in real time environmental or process monitoring applications, for example. In some embodiments the apparatus and method are well suited for detecting ions derived from other chemical separation methods, such as for example, gas or liquid chromatography methods. An enhanced ability to monitor a plurality of transient signals is provided, as the apparatus may be set to detect a plurality of pre-selected ion species, and it is not necessary to coordinate separation to detect the selected ion species of interest.

The apparatus may provide for improved speed and sensitivity for FAIMS analyses at a manufacturing cost comparable to a conventional FAIMS instrument. The use of a single ion source and single waveform generator are features that conserve manufacturing costs. Not only is performance enhanced at a comparable cost, but also the substantially simultaneous detection of multiple ion species of different mobility reduces ion discrimination due to environmental changes during the analysis and facilitates comparison of relative abundances of ion species.

Figure 2:
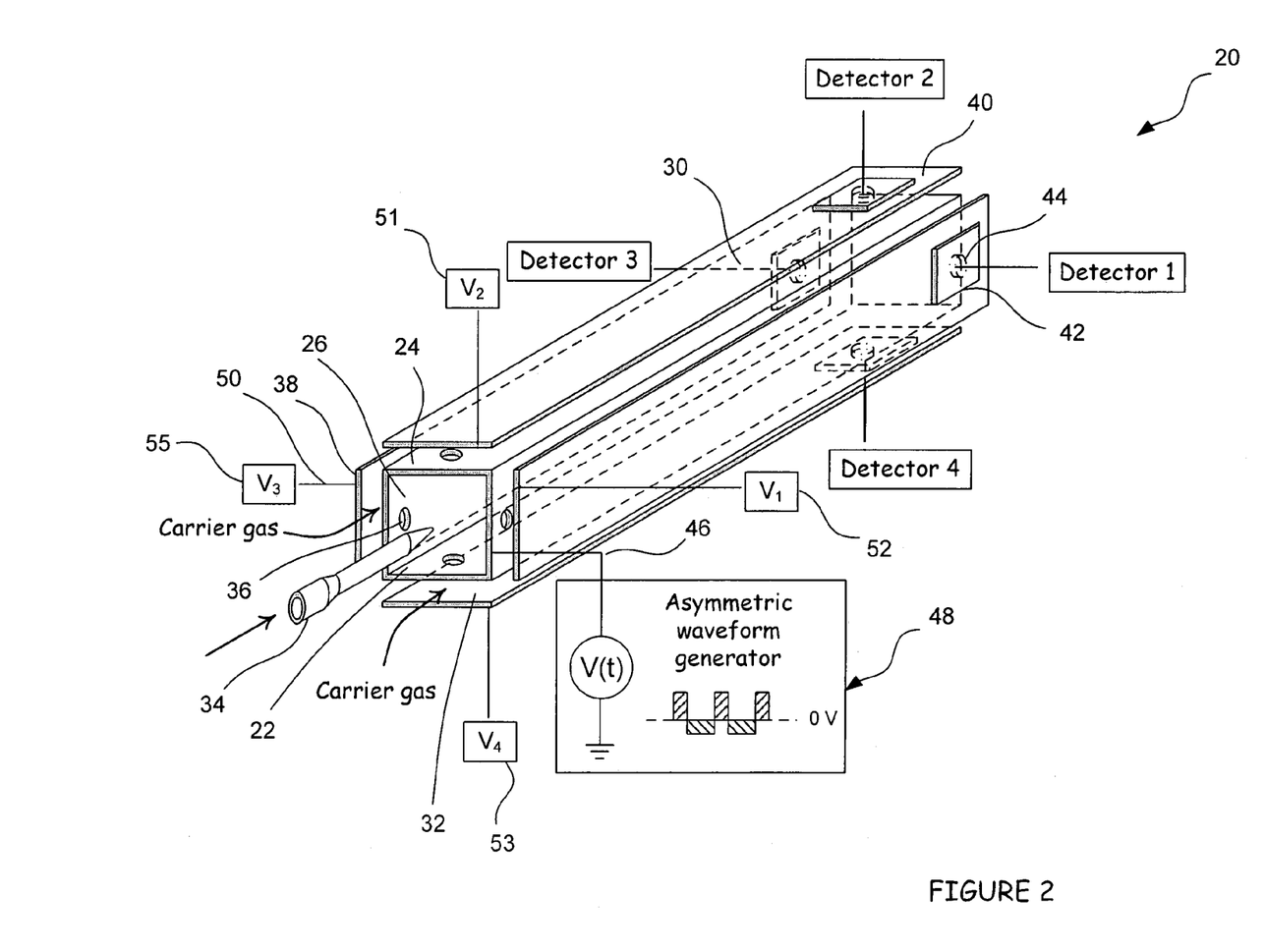
FIG. 2 is a perspective view of a multi-channel FAIMS spectrometer having a rectangular hollow electrode.

FIG. 2 shows an exemplary embodiment. In the embodiment shown in FIG. 2, the apparatus 20 comprises a hollow electrode 22 having an polygonal external surface 24 and a central region 26. The polygon shown in FIG. 2 is rectangular, however, other polygon shapes are likewise suitable for use in the practice of the invention. Four plate electrodes 30 are arranged around, parallel with, and distanced from the external surface 24 the hollow electrode 22.

For the embodiment of FIG. 2, in which the plate electrodes 30 are planar, each planar plate electrode 30 is sized and positioned such that a given planar plate electrode 30 is similar in dimensions to and aligned with one of the sides of the polygon of the polygonal hollow electrode 22. Thus, for the embodiment of FIG. 2 in which the hollow electrode 22 has four sides, four planar plate electrodes are used. Between each planar electrode 30 and each side of the external surface 24 of the hollow electrode 22 an ion channel 32 is formed (e.g., four "channels" or ion channels 32 are formed in the apparatus shown in FIG. 2). Each ion channel 32 is similar to the single ion channel 5 of the conventional FAIMS apparatus 1 shown in FIG. 1. Accordingly, each ion channel 32 can be operated as an ion mobility spectrometer; and for the embodiment shown in FIG. 2, four different ion species can be monitored simultaneously. The apparatus further includes an ion source 34 which provides ions to the central region 26 of the hollow electrode 22. Ions generated in the ion source 34 may be transferred into the central region 26 of the hollow electrode 22 by applying a potential difference between the ion source 34 and the hollow electrode 22.

A plurality of ion entrance apertures 36 are positioned in the hollow electrode 22. The plurality of ion entrance apertures 36 permit the transfer of sample ions from the central region 26 to the plurality of ion channels 32. Preferably the ion entrance apertures 36 are positioned at a first end 38 of the apparatus 20 adjacent the area in which ions are introduced into the central region 26 from the ion source 34.

Transfer of sample ions into the ion channels 32 is facilitated by the flow of a carrier gas in the ion channels 32. The carrier gas flows in the ion channels 32 in a direction from the first end 38 of the apparatus 20 to a second end 40 of the apparatus 20. The carrier gas is the gas in which the ion mobility is to be measured. The carrier gas may be admitted via a conventional valving in system or by any other system that permits reproducible regulation of the flow of the carrier gas. Carrier gases suitable for use in conventional FAIMS systems are likewise suitable for use in the multi-channel FAIMS systems described herein.

The apparatus 20 further comprises a detection system 42. The detection system 42 may be positioned in line with the ion channels 32 or off-axis as shown in FIG. 1. For off-axis detection, an exit aperture 44 may be provided in each planar electrode 30. The detection system 44 includes provision for detecting ions traveling through each ion channel 32. The detection system 44 may be an integrated system collecting data from all ion channels 32, or independent detectors for each ion channel 32, or a combination with a portion of the detectors stand alone and a portion of the detectors integrated. In the apparatus shown in FIG. 2, the detection system 44 comprises four independent detectors (e.g., detector 1, detector 2, detector 3, detector 4)—one for each ion channel 32. Alternatively, a detection system in which a single detector can collect ion information from multiple points such as a plurality of ion channels may be employed, for example. The detection system 44 must be able to detect the presence of an ion species and/or collect ions. Suitable detectors for detecting ion species include but are not limited to faraday cups, faraday cups with amplification systems, diode arrays, and charge induced devices (CID), for example. Alternatively, the detection system 44 may collect ions and transfer them for an additional stage of analysis. For example, the detection system 44 may collect ions for transfer to and/or serve as an inlet for a second stage ion analyzer such as a mass spectrometer or second ion mobility spectrometer, for example. A subsequent mass spectrometry analysis may provide further structural characterization of the ion species and/or quantitative data, for example. In some applications the detection system 44 may include a combination of detection devices. For example, a simple detection device such as a faraday cup might be used for detecting ion species passing through one or more of the ion channels 32 while ions passing through one or more other ion channels 32 may be directed into a second stage ion analyzer.

The apparatus 20 further comprises a hollow electrode contact 46 and plurality of plate electrode contacts 50. The hollow electrode contact 46 permits application of a high voltage asymmetric waveform to the hollow electrode 22. The asymmetric waveform is produced by an asymmetric waveform generator 48. Application of the asymmetric high voltage waveform creates an electric field in the ion channels 32.

Each of the plate electrodes 30 has a plate electrode contact 50. The plate electrode contacts 50 provide for the application of a compensation voltage from a compensation voltage source 51, 52, 53, 55 to each of the plate electrodes 30. The compensation voltage sources may be power supplies, for example. The provision of a compensation voltage to a given plate electrode 30 should be independently controllable in magnitude and duration from the compensation voltage applied to any of the other of the plurality of plate electrodes 30. Independent control of the compensation voltage applied to each plate electrode 30 permits a different species of ion to be analyzed in each of the plurality of ion channels 32 simultaneously. Further independent control of the duration of compensation voltage to a given plate electrode 30 provides for the ability to change the ion species selected in a given channel 32 without changing the ion species monitored in another of the plurality of ion channels 32. Optionally, one or more of the compensation voltages can be scanned while other compensation voltages are set to pass a selected ion which provides for simultaneous monitoring of selected ions while obtaining scan data for the sample.

Figure 3:
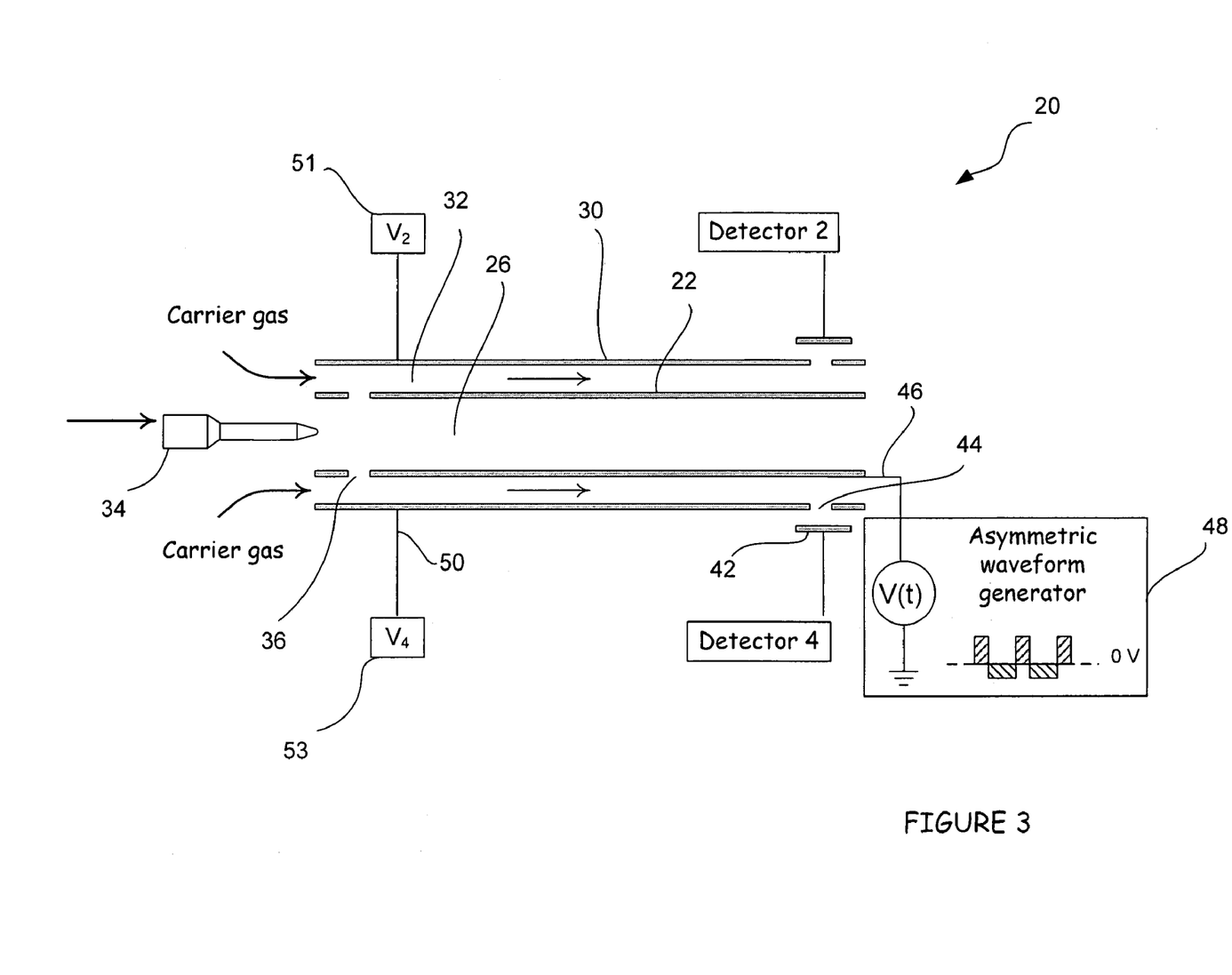
FIG. 3 is a schematic cross sectional view of a multi-channel FAIMS spectrometer in which the cross section is parallel to the direction of the carrier gas flow.

FIG. 3 is a cross sectional schematic diagram of the embodiment shown in FIG. 2. As the diagram of FIG. 3 is a schematic diagram, only two of the four plate electrodes 30 and two ion channels 32 are shown. In the embodiment of FIGS. 2 and 3 the hollow electrode 22 is a four sided polygon and four plate electrodes 30 are positioned parallel to and distanced from each side of the polygon. A four-sided polygon is exemplary. The hollow electrode 22 may have any polygon shape.

Figure 4:
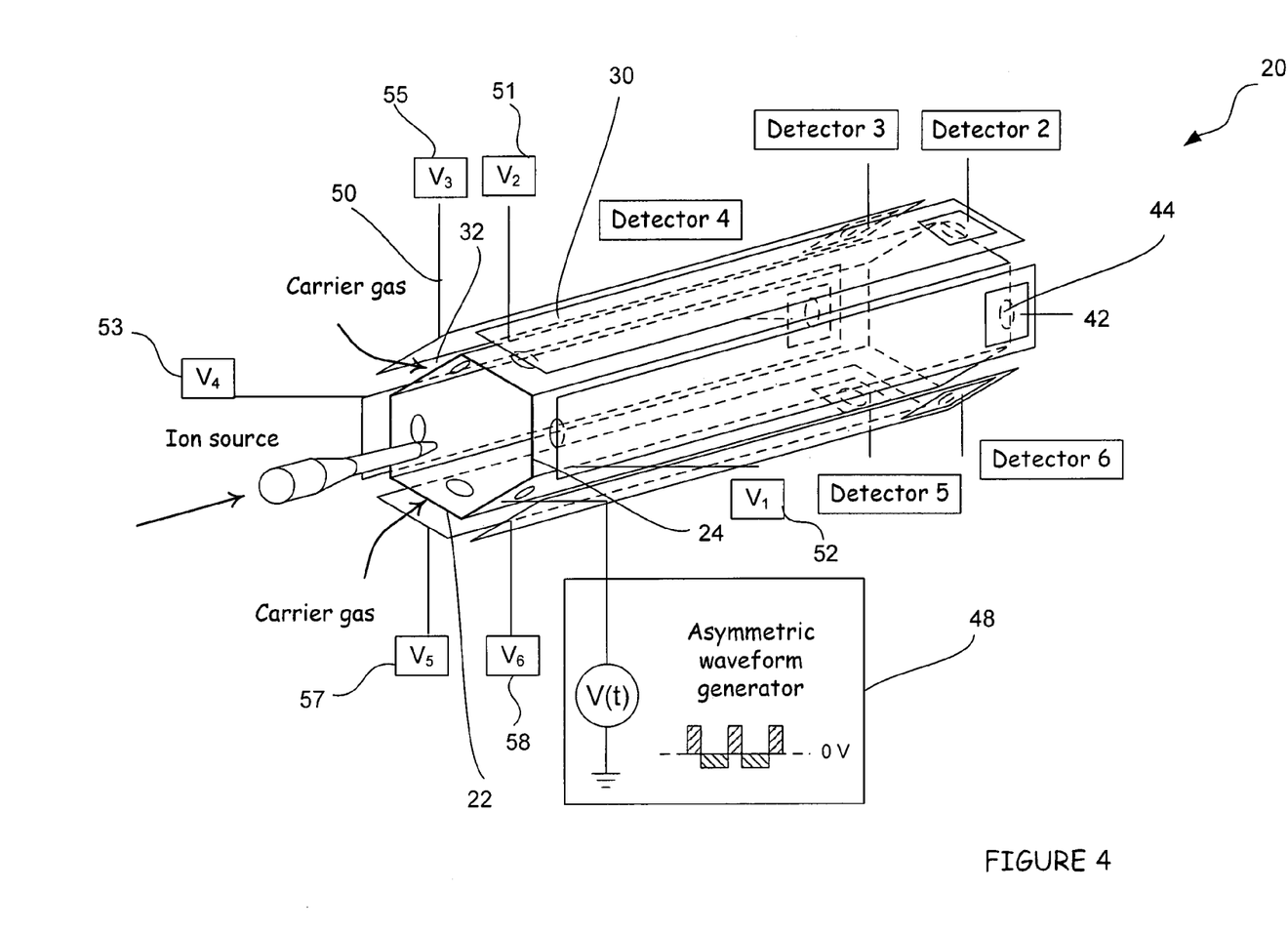
FIG. 4 is a perspective view of a multi-channel FAIMS spectrometer having a hexagonal hollow electrode.

FIG. 4 shows an exemplary embodiment in which the hollow electrode 22 is a six-sided polygon. In the embodiment of FIG. 4, a plate electrode 30 is positioned parallel to and distanced from each of the six faces of the six-sided hollow electrode 22. A plate electrode contact 50 is provided to each plate electrode 30 to connect that plate electrode 30 to an independently controllable compensation voltage source 51, 52, 53, 55, 57, 58.

Typically, for embodiments in which the hollow electrode is a polygon, a planar electrode 30 is paired with each side of the polygon to produce a plurality of ion channels equal in number to the number of sides of the polygon. This is not required, but as a practical matter desirable to provide the maximum number of ion channels for the configuration. Further, the number of sides of the polygonal hollow electrode 22 will typically be 4-8. Greater numbers of sides and ion channels 32 are possible so long as the plate electrodes can be electrically isolated from each other. However, greater numbers of channels may present some practical challenges such as, for example, difficulty in maintaining sufficient sample size and forming substantially discrete channels.

Figure 5:
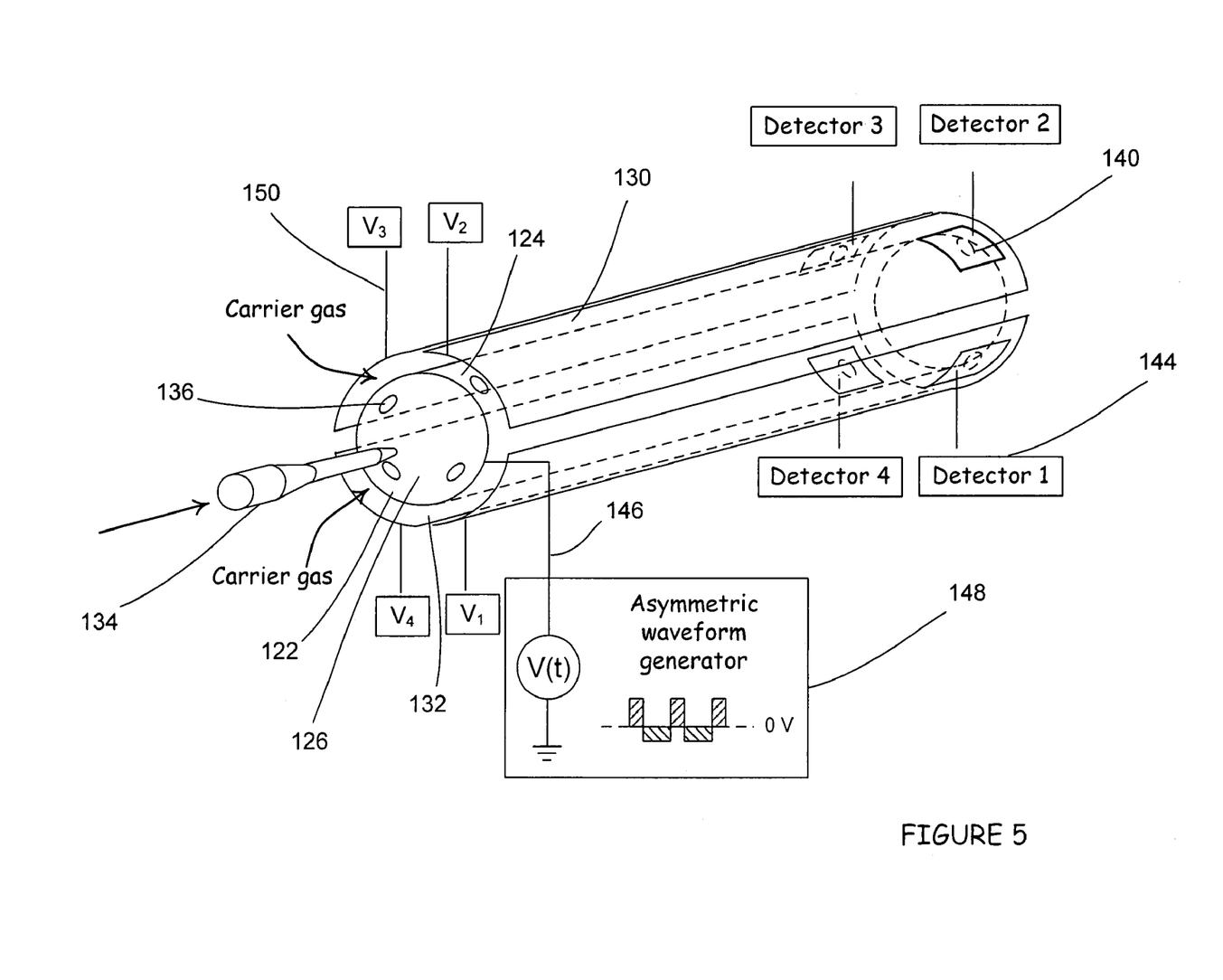
FIG. 5 is a perspective view of a multi-channel FAIMS spectrometer having a cylindrical hollow electrode and curved plate electrodes.

Another embodiment of the multi-channel FAIMS apparatus is shown in FIG. 5. The embodiment shown in FIG. 5 has a cylindrical hollow electrode 122 with an external surface 124. A plurality of curved plate electrodes 130 are arranged parallel to and distanced from the external surface 124 of the cylindrical hollow electrode 122. A plurality of ion channels 132 are formed wherein one ion channel is formed between each curved plate electrode 130 and the cylindrical hollow electrode 122. Each curved plate electrode 130 should be electrically isolated from the other curved plate electrodes 130. An asymmetric waveform is applied via a hollow electrode contact 146 to the cylindrical hollow electrode 122. The applied asymmetric waveform creates an electric field in the ion channels 132. A plurality of curved electrode contacts 150 are provided for applying a compensation voltage to each of the plurality of curved electrodes 130. The compensation voltage applied to each of the plurality of curved electrodes 130 is independently adjustable.

An ion source 134 is provided to introduce ions into a central region 126 of cylindrical hollow electrode 122.

A potential differential between the ion source 134 and the cylindrical hollow electrode 122 may be used to transfer ions into the central region 126 of the cylindrical hollow electrode 122. A plurality of entrance apertures 136 permit ions to flow into the ion channels 132. A plurality of exit orifices 140 permit ions to depart the ion channel 134 for detection by the detection system 144.

Ionization sources, detector systems, carrier gases, asymmetric wave generators, compensation voltage generators suitable for use in the polygonal hollow electrode FAIMS apparatus (see FIGS. 2-4) and/or conventional FAIMS are likewise suitable for use in the apparatus 20 with a cylindrical hollow electrode 122. Any number of curved plate electrodes 130 may be used so long as ion transmission sufficient for analysis is maintained and the curved plate electrodes 130 are electrically isolated from each other.

Figure 6:
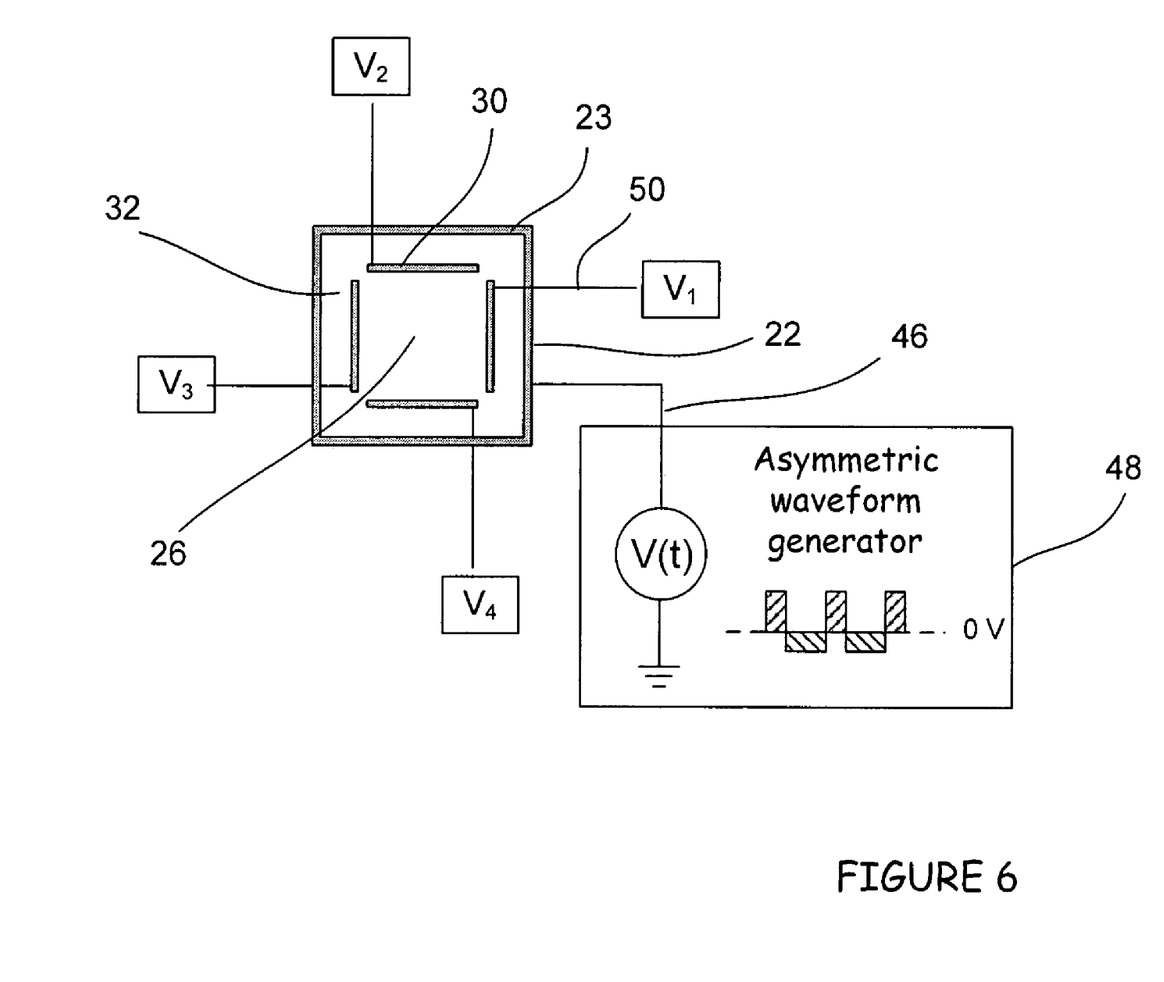
FIG. 6 is a schematic cross section view perpendicular to the direction of the carrier gas flow of a multi-channel FAIMS in which the plurality of plate electrodes are located within the central region of the hollow electrode.

Alternatively, as shown in FIG. 6, which is a schematic diagram of a cross section perpendicular to the direction flow in the apparatus 20, the plate electrodes 30 may be located in the central region 26 of the hollow electrode 22. In this embodiment, the plate electrodes 30 are aligned parallel to and distanced from an inner surface 23 of the hollow electrode 22. Accordingly, ion channels 32 are formed in a portion of the central region 26 of the hollow electrode 22 between the inner surface 23 of the hollow electrode 22 and the plate electrodes 30. The hollow electrode 22 may have either a polygonal or cylindrical shape. If a polygonal shape is used for the hollow electrode 22, the plate electrodes 30 would be planar. Alternatively, curved plate electrodes 30 with a curvature that would provide for parallel alignment would be used with a cylindrical hollow electrode 30. A detector or detectors (not shown in the cross sectional diagram of FIG. 6) may be positioned external to the hollow electrode 22 in line with the ion channels 32 or alternatively off-axis with respect to the ion channels 32. For off-axis detection, apertures may be provided in the hollow electrode 22 to permit transfer of ions to the detector(s). Optionally, the detector(s) may be positioned internally adjacent the plate electrodes 30 with apertures in the plate electrodes 30 to permit transfer of the ions to the detection system 144. Alternatively, some combination of detector positioning may be employed. It is not necessary that detectors for all ion channels be positioned in similar positions and/or that the same type of detector and or same detection system is used for all ion channels 32.

The FIGS. 2-6 show symmetrical structures for the apparatus 20. A symmetrical structure is not required. For example, the different separation channels 32, 132 of a given apparatus can have different lengths or widths and/or employ entrance and exit apertures of different dimensions and/or relative positions.

As to construction, the hollow electrode 22, 122 and plate electrodes 30, 130 can be constructed from a conductive material or non-conductive material with conductive plating or some combination thereof. The plate electrodes can be made as an integrated structure so long as the conductive region that forms a given plate electrode 30, 130 is electrically isolated from other plate electrodes 30, 130. Micro-machining may be employed to facilitate construction of the electrically isolated plate electrode 30, 130.

For all embodiments shown ions may be analyzed similarly. Ions generated from an ion source 34, 134 are introduced into the hollow electrode 22, 122. Ions may be derived from a variety of sources including but not limited to ionization of a sample in a device such as an electrospray ionization source, atmospheric pressure chemical ionization source (APCI), atmospheric pressure ionization source (API), atmospheric pressure MALDI (matrix assisted laser desorption ionization) source, a discharge source, a radioactive ionization source, fast atom bombardment source, and SIMS source. The sample may be introduced into the ion source by a direct probe or infusion pump. Alternatively, the sample may be introduced into the source as effluent from a gas or liquid chromatograph, or ions transported in a gas stream from an environmental or process monitoring sample. Typically, the ions introduced into the FAIMS apparatus are a mixture of ion species. A potential differential between the ion source 34, 134 and the hollow electrode 22, 122 facilitates transfer of ions into the central region 26, 126 of the hollow electrode 22, 122.

Ions may be transferred from the central region 26, 126 of the hollow electrode 22, 122 to the plurality of ion channels 30, 130 via the plurality of entrance apertures 36, 136. Typically a mixture of ion species are present when the sample ions are introduced into the ion channel 32, 132. Entrance of ions into the ion channels 30, 130 and transport through the ion channels 32, 132 is facilitated by a carrier gas flowing in the direction from the first end 38 near the ion source toward a second end 40 of the apparatus 20. Typically, the detection system 44 is positioned proximate the second end 40.

The carrier gas not only facilitates transport of ions but also mediates the motion of ions through the ion channels. Typically gases such as $CO_2$, nitrogen, oxygen are used as the carrier gas. Also mixtures of gases may be used. Defined identity of the gas composition as well as an apparatus for regulating and measuring flow rate of the carrier gas are desirable, as such factors and parameters facilitate reproducibility of analyses.

When a sample is present for analysis in the FAIMS apparatus, a high filed asymmetric waveform is applied to the hollow cylinder electrode 22, 122. The high field asymmetric waveform should be sufficient to effect a net displacement between a first and a second ion species of the plurality of ion species in an aliquot of sample ions in the time of one cycle of the applied asymmetric waveform. Typically, voltages >5000 volts/cm are used. A compensation voltage is applied to two or more plate electrodes 30, 130. When multichannel analysis is performed, typically a different compensation voltage is applied to each plate electrode to permit transfer of a different ion species in each ion channel. This is not required. For example, in some applications in which a combination of detector types are used, two channels may transmit the same ion species to two different detectors such as, for example, to a faraday cup and a mass spectrometer. Typically, the asymmetric waveform voltage and compensation voltages are predetermined to permit the transfer of a selected ion species in a predetermined ion channel 30, 130. By selecting different compensation voltages to each plate electrode 30, 130, different ion species are transmitted in the selected ion channels 30, 130. Only the ions species compatible with the selected compensation voltage will pass the length of selected ion channel 30 and reach the detection system 44, 144. Detection of the different ion species that pass through each of the channels occurs substantially simultaneously.

Each ion channel 32, 132 of the plurality of ion channels 32, 132 operates as FAIMS analyzer. Each ion channel 32, 132 can analyze a selected ion simultaneously with the analysis of different ion species other ion channels 32, 132 of the plurality of ion channels. However, all ion channels 32, 132 can use ions generated from the same sample in the ion source at the same time which facilitates comparisons of ion species, efficient use of sample, typically reduces the amount of sample needed, and increases speed of analysis when multiple ion species are of interest.

The detection systems 44, 144 for each ion channel 32, 132 may operate independently. Alternatively, ion signals from the detector for each ion channel 32, 32 can be collected by a processing device and processed separately or the signals can be processed collectively using an appropriate computer algorithm. Optionally, a combination of independent detection systems 44, 144 for selected channels and interlinked detection systems 44, 144 for other channels 32, 132 maybe used. In some embodiments the detection system 44, 144 may include apparatus for an additional stage of ion analysis such as a second stage of ion mobility spectrometry or a mass spectrometry, for example. When a mass spectrometer is used it may be operated to analyze ions passing through one or more ion channels 32, 132 over time or alternatively configured to analyze ions from a plurality of ion channels 32, 132 using, for example, selected ion monitoring mass spectrometry analysis.

In some embodiments the compensation voltage to one or more selected plate electrodes 30, 130 may be changed to select a different ion species while maintaining the compensation voltage to other plate electrodes 30, 130 to continue analyses of a previously selected ion species. In other embodiments it may be desirable to fix the compensation voltage to selected plate electrodes 30, 130 to monitor selected ion species and scan the compensation voltage to one or more plate electrodes to profile the composition of the sample or a selected group of components of the sample. Typically, different ion species are analyzed or different types of analyses are done in each ion channel 32, 132 but this is not required. For example, when two different types of detectors are used in the detection system 44, 144, selecting the same ion species in two channels and detecting the ion species with different detection systems 44, 144 in each ion channel permits real time comparisons.

The foregoing discussion discloses and describes many exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

The invention claimed is:

1. An apparatus for separating ions, comprising:
    (a) an analyzer region comprising a hollow electrode and a plurality of plate electrodes, the hollow electrode having an external surface and a central region, the plate electrodes positioned parallel to and distanced from the external surface of the hollow electrode, wherein a channel is formed between each plate electrode of the plurality of plate electrodes and the hollow electrode;
    (b) a contact for applying an asymmetric waveform to the hollow electrode; and
    (c) a plurality of contacts for applying a compensation voltage to the plurality of plate electrodes wherein the compensation voltage is independently adjustable to each of the plurality of plate electrodes.

2. The apparatus of claim 1, further comprising an ion source in operable relation to the analyzer region.

3. The apparatus of claim 2, further comprising a plurality of entrance apertures in the hollow electrode, wherein the entrance apertures are positioned for transfer of ions from the central region of the hollow electrode to each of the plurality of ion channels.

4. The apparatus of claim 1, further comprising a detection system in communication with the analyzer region.

5. The apparatus of claim 4, further comprising a second stage ion analyzer.

6. The apparatus of claim 4, wherein the detection system detects a plurality of ion species substantially simultaneously.

7. The apparatus of claim 1, wherein the external surface of the hollow electrode has a polygon shape with a plurality of sides and each of the plurality of the sides is substantially aligned with one of the plurality of planar plate electrodes.

8. The apparatus of claim 1, wherein the hollow electrode is cylindrical and the plate electrodes are curved plate electrodes.

9. An apparatus for separating ions comprising a high field asymmetric waveform ion mobility spectrometer including:
    (a) an analyzer region comprising a hollow electrode and a plurality of plate electrodes, the hollow electrode having an internal surface surrounding a central region, the plate electrodes positioned in the central region, parallel to and distanced from the internal surface of the hollow electrode, wherein an ion channel is formed between each plate electrode of the plurality of plate electrodes and the hollow electrode;
    (b) a contact for applying an asymmetric waveform to the hollow electrode; and
    (c) a plurality of contacts for applying a compensation voltage to the plurality of plate electrodes wherein the compensation voltage is independently adjustable to each of the plurality of plate electrodes.

10. The apparatus of claim 9, further comprising an ion source in communication with the analyzer region.

11. The apparatus of claim 9, further comprising a detection system in communication with the analyzer region.

12. The apparatus of claim 11, wherein the detection system detects a plurality of ion species substantially simultaneously.

13. The apparatus of claim 11, further comprising a second stage ion analyzer.

14. A method for separating ions comprising the steps of:
    (a) providing a plurality of ion species;
    (b) providing an analyzer including an analyzer region comprising a hollow electrode and a plurality of plate electrodes arranged parallel to and distanced from the hollow electrode, wherein a channel is formed between each plate electrode and the hollow electrode;
    c) providing a high voltage asymmetric waveform to the hollow electrode to generate a field in the plurality of channels between the hollow electrode and the plurality of plate of electrodes;
    d) providing a first compensation voltage to a first plate electrode of the plurality of plate electrodes and a second compensation voltage to a second plate electrode of the plurality of electrodes wherein the first compensation voltage is different than the second compensation voltage;
    e) setting the high voltage asymmetric waveform in order to effect a difference in net displacement between a first and a second ion species of the plurality of ion species in the field in the time of one cycle of the applied asymmetric waveform; and
    f) setting the compensation voltage of the first plate electrode of the plurality of plate electrodes to a determined value to support transmission of the first ion species through a first channel between the first plate electrode and the hollow electrode and setting the second compensation voltage to the second plate electrode to support transmission of a second ion species through a second channel between the second plate electrode and the hollow electrode.

15. The method of claim 14, wherein the plurality of ion species are produced in an ion source and further comprising transmitting the a portion of the plurality of ion species into the plurality of channels with a carrier gas.

16. The method of claim 14, further comprising detecting the first and the second ion species after transmission though the first and the second channels.

17. The method of claim 16, wherein detection of the first and second ion species occurs substantially simultaneously.

18. The method of claim 14, wherein a discrete compensation voltage is applied to each plate electrode of the plurality of electrodes thereby providing for transmission of a different ion species of the plurality of ion species in each of the plurality of channels.

19. The method of claim 14, further comprising adjusting the compensation voltage applied to the first channel electrode to provide for transmission of an ion species of the plurality of ion species other than the first ion species.

20. The method of claim 14, further comprising transmitting selected ions to a second stage ion analyzer.

21. The method of claim 14, wherein the hollow electrode has an external surface and the plurality of plate electrodes are positioned parallel to and distanced from the external surface of the hollow electrode, and wherein the channel is formed between each plate electrode of the plurality of plate electrodes and the external surface of the hollow electrode.

22. The method of claim 14, wherein the hollow electrode has an internal surface and the plurality of plate electrodes are positioned parallel to and distanced from the internal surface of the hollow electrode, and wherein the channel is formed between each plate electrode of the plurality of plate electrodes and the internal surface of the hollow electrode.

* * * * *